US008691201B2

(12) United States Patent
Tanaka et al.

(10) Patent No.: US 8,691,201 B2
(45) Date of Patent: Apr. 8, 2014

(54) DEODORANT MATERIAL

(75) Inventors: Toshihiro Tanaka, Shiga (JP); Hirokuni Inoue, Osaka (JP); Hironori Ishiwata, Osaka (JP)

(73) Assignee: Toray Opelontex Co., Ltd., Tokyo (JP)

( * ) Notice: Subject to any disclaimer, the term of this patent is extended or adjusted under 35 U.S.C. 154(b) by 0 days.

(21) Appl. No.: 12/867,547

(22) PCT Filed: Feb. 13, 2009

(86) PCT No.: PCT/JP2009/052360
§ 371 (c)(1),
(2), (4) Date: Sep. 15, 2010

(87) PCT Pub. No.: WO2009/101995
PCT Pub. Date: Aug. 20, 2009

(65) Prior Publication Data
US 2011/0033409 A1    Feb. 10, 2011

(30) Foreign Application Priority Data

Feb. 15, 2008   (JP) .................................. 2008-035223

(51) Int. Cl.
  *A61L 9/01*   (2006.01)
  *C08G 18/00*  (2006.01)
  *A61K 31/715* (2006.01)

(52) U.S. Cl.
  USPC ............ 424/76.1; 424/400; 424/65; 523/201; 359/534

(58) Field of Classification Search
  USPC ............ 424/76.1, 400, 65; 523/201; 359/534
  See application file for complete search history.

(56) References Cited

U.S. PATENT DOCUMENTS

| | | | | |
|---|---|---|---|---|
| 2,187,163 | A | * | 1/1940 | Langer .................... 15/104.93 |
| 5,487,942 | A | * | 1/1996 | Gomibuchi ................... 428/364 |
| 5,784,198 | A | * | 7/1998 | Nagaoka ....................... 359/534 |
| 6,214,145 | B1 | * | 4/2001 | Umezawa et al. ............ 156/167 |
| 6,486,238 | B1 | * | 11/2002 | Kitamura et al. ............. 524/100 |
| 6,911,502 | B2 | * | 6/2005 | Vedula ......................... 525/457 |
| 2001/0031249 | A1 | * | 10/2001 | Oku et al. ........................ 424/65 |
| 2001/0053803 | A1 | | 12/2001 | Kuwahara et al. |
| 2006/0127335 | A1 | * | 6/2006 | Nakamura ...................... 424/65 |
| 2010/0297053 | A1 | * | 11/2010 | Hirukawa .................... 424/76.1 |
| 2011/0031249 | A1 | * | 2/2011 | Thelen .......................... 220/315 |

FOREIGN PATENT DOCUMENTS

| | | |
|---|---|---|
| EP | 0 431 262 | 8/1990 |
| EP | 1 595 918 | 11/2005 |
| JP | 2007-204686 | 8/2007 |
| WO | 2005/026431 | 3/2005 |
| WO | WO 2007/088879 | * 9/2007 |

OTHER PUBLICATIONS

Supplementary European Search Report dated Mar. 25, 2011 in European Application No. EP 09 70 9799.
English translation of the International Preliminary Report on Patentability and Written Opinion dated Oct. 5, 2010.
B. Hua et al., "Microphase Separation of Carboxylic Polyurethaneurea Emulsions", China Synthetic Rubber Industry, vol. 19, No. 5, pp. 281-283, 1996 (English Abstract).
B. Hua et al., "Preparation and Characterization of Self-Emulsifying Polyurethane-Urea Emulsion", China Synthetic Rubber Industry, vol. 19, No. 2, pp. 81-83, 1996, with English Abstract.
International Search Report issued May 12, 2009 in International (PCT) Application No. PCT/JP2009/052360.

* cited by examiner

*Primary Examiner* — Anoop Singh
*Assistant Examiner* — Anna Falkowitz
(74) *Attorney, Agent, or Firm* — Wenderoth, Lind & Ponack, L.L.P.

(57) ABSTRACT

An object of the present invention is to provide a deodorant material having an excellent capability of removing an odor, especially a distinctive body odor of the middle-aged and elderly. The deodorant material comprises a polyurethane resin capable of removing the odor of nonenal, preferably further capable of removing the odor of at least one selected from the group consisting of ammonia, acetic acid, and isovaleric acid.

8 Claims, No Drawings

DEODORANT MATERIAL

This application is a U.S. national stage of International Application No. PCT/JP2009/052360 filed Feb. 13, 2009.

TECHNICAL FIELD

The present invention relates to a deodorant material having a remarkably excellent capability of removing the odor of nonenal, which is one of odor components of a distinctive body odor of the middle-aged and elderly.

BACKGROUND ART

In recent years, people have been in pursuit of more and more comfort in daily life, and deodorant materials have attracted attention accordingly.

For example, a modified cellulose fiber obtained by graft-copolymerizing a cellulose fiber such as a cotton fiber with methacrylic acid is known as a deodorant material having an excellent capability of removing a foul odor such as an ammonia odor and a urine odor (for example, see JP-A-6-184941). As our society is aging, there is a growing demand for deodorizing capabilities, in particular, a capability of removing a distinctive body odor of the middle-aged and elderly. The distinctive body odor of the middle-aged and elderly is generally considered to consist of the following odor components: ammonia, acetic acid, isovaleric acid, and nonenal. According to evaluation criteria in "the Certification Criteria of Deodorant-finished Textiles" established by Japan Textile Evaluation Technology Council (JTETC), in order to remove the distinctive body odor of the middle-aged and elderly, it is required for a deodorant material to have a function of decreasing all the odor components: ammonia, acetic acid, isovaleric acid, and nonenal.

Various attempts have been made in order to obtain a deodorant material having various kinds of deodorizing capabilities. For example, a fabric knitted from a raw fiber to which a photo-catalytic titanium oxide is attached (for example, see JP-A-2002-030552) and a method of finishing a fabric product by immersing the product in a treatment solution containing a photocatalyst (for example, see JP-A-2007-126764) are known.

As far as the applicants know, however, no deodorant material having an excellent capability of removing the odor of nonenal or the distinctive body odor of the middle-aged and elderly has yet been reported.

SUMMARY OF INVENTION

Technical Problem

As mentioned above, no deodorant material having a satisfactory capability of removing the odor of nonenal or the distinctive body odor of the middle-aged and elderly has yet been reported. In view of the problems of the conventional art mentioned above, an object of the present invention is to provide a deodorant material having an excellent capability of removing an odor, in particular, the distinctive body odor of the middle-aged and elderly.

Solution to Problem

The inventors of the present invention found, in the process of developing an excellent deodorant material, that a polyurethane resin can exhibit a surprising capability of removing the odor of nonenal, which is one of odor components of the distinctive body odor of the middle-aged and elderly. The inventors did extensive development based on the finding and the present invention was thus completed.

That is, the present invention comprises the following constitution.

(1) A deodorant material comprising a polyurethane resin capable of removing the odor of nonenal.

(2) The deodorant material according to (1), wherein the polyurethane resin is further capable of removing the odor of at least one selected from the group consisting of ammonia, acetic acid, and isovaleric acid.

(3) The deodorant material according to (1) or (2), wherein the glass transition point (Tg) of the polyurethane resin is −100 to 0° C.

(4) The deodorant material according to any of (1) to (3), wherein the polyurethane resin is a polyurethane urea fiber.

(5) The deodorant material according to any of (1) to (4), wherein the deodorant material further comprises a fiber containing a carboxyl group.

(6) The deodorant material according to (5), wherein the fiber containing a carboxyl group has a concentration of carboxyl group of 30 to 3000 meq/kg.

(7) The deodorant material according to (5), wherein the fiber containing a carboxyl group is a cellulose fiber graft-polymerized with 2 to 30% by weight of a hydrophilic vinyl monomer.

(8) A use of a polyurethane resin for producing a deodorant material capable of removing the odor of nonenal.

A preferable embodiment of the polyurethane resin used for the deodorant material of the present invention is a stretch fabric as described below.

(1') A stretch fabric comprising, relative to the weight of the fabric, 99 to 70% by weight of a spun yarn (A), 1 to 30% by weight of a polyurethane elastic fiber (B), and an antimicrobial agent, which is exhausted by or loaded on the fabric, the spun yarn (A) comprising, relative to the weight of the spun yarn, 100 to 5% by weight of a cellulose fiber containing a carboxyl group, and 0 to 95% by weight of a polyester fiber.

(2') The stretch fabric according to (1'), wherein the cellulose fiber containing a carboxyl group is a modified cellulose fiber obtained by graft-copolymerizing a cellulose fiber with methacrylic acid.

(3') The stretch fabric according to (1') or (2'), wherein the spun yarn is obtained by one or more production methods selected from the group consisting of ring traveler spinning, open end spinning, binding spinning, and twist spinning.

(4') The stretch fabric according to any of (1') to (3'), wherein the polyester fiber has a fiber surface area of about 0.1 m$^2$ or more per gram, or a single fiber fineness of about 3 deniers or less.

(5') The stretch fabric according to any of (1') to (4'), wherein the concentration of urethane group in a polyurethane constituting the polyurethane elastic fiber is about 0.2 to 3.5 mol/kg.

(6') The stretch fabric according to any of (1') to (5') wherein the polyurethane elastic fiber comprises a polyurethane urea obtained by polymerizing a polyalkylene ether diol comprising 5 to 25 mol % of the following structural unit (a) and 95 to 75 mol % of the following structural unit (b) and having a number average molecular weight of 250 to 10000, with a diisocyanate compound, and a diamino compound.

Formula 1

Structural unit (a):

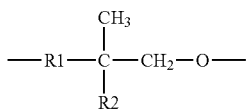

Structural unit (b):

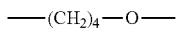

(wherein R1 represents a straight-chain alkylene group having 1 to 3 carbon atoms, and R2 represents hydrogen or an alkyl group having 1 to 3 carbon atoms)

(7') The stretch fabric according to any of (1') to (6'), wherein the concentration of effective terminal amine in a polyurethane constituting the polyurethane elastic fiber is 15 to 50 meq/kg.

(8') The stretch fabric according to any of (1') to (7'), wherein the antimicrobial agent is one or more selected from the group consisting of an organic nitrogen-sulfur compound, a quaternary ammonium compound, a phosphoric ester compound, and an inorganic compound containing a metal ion.

(9') The stretch fabric according to any of (1') to (8'), wherein the stretch fabric has a fabric weight of 100 to 1000 g/m² and an elongation rate in the longitudinal and/or lateral direction of 5% or more.

(10') The stretch fabric according to any of (1') to (9'), wherein the spun yarn has an English cotton count of 6 to 60.

(11') The stretch fabric according to (1') to (10'), wherein the pH of a treatment solution containing the antimicrobial agent used for a treatment where the fabric exhausts or is loaded with the antimicrobial agent is 5.0 to 6.0.

Advantageous Effects of Invention

A deodorant material of the present invention has a capability of removing an odor, in particular, a distinctive body odor of the middle-aged and elderly, and further has a surprisingly lasting, significant effect of removing the odor of nonenal, which is a component of the distinctive body odor of the middle-aged and elderly.

DESCRIPTION OF EMBODIMENTS

Preferable embodiments of the present invention will be explained below.

First, a polyurethane resin used in the present invention will be explained.

A polyurethane resin used in the present invention may be any polyurethane resin and not specifically limited as long as the main component of the polyurethane resin comprises a polymer diol and a diisocyanate. The synthetic method of the polyurethane resin is also not specifically limited. The main component refers to a component that accounts for 50% by weight or more of components that form the polyurethane resin.

That is, for example, the polyurethane resin may be a polyurethane urea comprising a polymer diol, a diisocyanate, and as a chain extender, a diamino compound (low molecular weight diamine), or a polyurethane comprising a polymer diol, a diisocyanate, and as a chain extender, low molecular weight diol. As the chain extender, a compound having a hydroxyl group and an amino group in the molecule may also be used. It is also preferable to use a polyfunctional glycol, an isocyanate, or the like having three or more functional groups as far as the polyfunctional glycol, the isocyanate, or the like does not prevent the effect of the present invention.

A typical structural unit constituting the polyurethane resin used in the present invention will be described here.

Preferable examples of the polymer diol, which is a structural unit constituting the polyurethane resin, include a polyether-based glycol, a polyester-based glycol, and a polycarbonate diol. In order to provide high elongation rate for the polyurethane resin, especially when the polyurethane resin is made into a flexible deodorant fiber, it is preferable to use a polyether-based glycol.

The polyether-based glycol preferably comprises a copolymerized diol compound comprising a unit expressed by the following general formula (I).

Formula 2

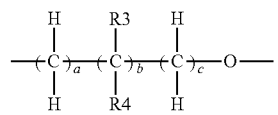

(I)

(wherein a and c represent an integer of 1 to 3, b represents an integer of 0 to 3, and R3 and R4 each represent a hydrogen atom or an alkyl group having 1 to 3 carbon atoms)

Specific examples of the polyether-based glycol compound include polyethylene glycol, modified polyethylene glycol, polypropylene glycol, polytrimethylene ether glycol, polytetramethylene ether glycol (hereinafter abbreviated to PTMG), modified PTMG that is a copolymer of tetrahydrofuran and 3-methyl-tetrahydrofuran, modified PTMG that is a copolymer of tetrahydrofuran and 2,3-dimethyl-tetrahydrofuran, modified PTMG that is a copolymer of tetrahydrofuran and neopentyl glycol, and a random copolymer in which tetrahydrofuran and ethylene oxide and/or propylene oxide are randomly arranged. As the polyurethane resin used in the present invention, these polyether-based glycols may be used alone, or in combination of two or more, as a mixture or a copolymer. Among these, it is particularly preferable to use PTMG or modified PTMG.

In order to increase abrasion resistance and light resistance of the polyurethane resin, it is preferable to use a polyester-based glycol such as butylene adipate, polycaprolactone diol, a polyester diol having a side chain obtained by polycondensating a mixture of 3-methyl-1,5-pentanediol and polypropylene polyol with adipic acid or the like; a polycarbonate diol containing a dicarboxylic acid ester unit derived from a dicarboxylic acid component comprising 3,8-dimethyldecanedioic acid and/or 3,7-dimethyldecanedioid acid, and a diol component; and the like.

These polymer diols may be used alone, or in combination of two or more, as a mixture or a copolymer.

Next, preferable examples of the diisocyanate, which is a structural unit constituting the polyurethane resin used in the present invention, include an aromatic diisocyanate, an alicyclic diisocyanate, and an aliphatic diisocyanate. Preferable examples of the aromatic diisocyanate include diphenylmethane diisocyanate (hereinafter abbreviated to MDI), tolylene diisocyanate, 1,4-diisocyanate benzene, xylylene diisocyanate, and 2,6-naphthalene diisocyanate, all of which are preferable especially for synthesizing a polyurethane having high heat resistance and high strength. Preferable examples of the alicyclic diisocyanate include methylenebis (cyclohexyl isocyanate), isophoronediisocyanate, methylcyclohexane-2,4-diisocyanate, methylcyclohexane-2,6-diisocyanate, cyclohexane-1,4-diisocyanate, hexahydroxylylenediisocyanate, hexahydrotolylene diisocyanate, and octahydro-1,5-naphthalene diisocyanate. The aliphatic diisocyanate can be effectively used especially for preventing the polyurethane from turning yellow. Among these, 4,4☐-MDI is particularly preferable. These diisocyanates may be used alone or in combination of two or more.

Next, as the chain extender, which extends the structural unit chain constituting the polyurethane resin, it is preferable to use at least one or more selected from low molecular weight diamines and low molecular weight diols. The chain extender may be a substance having both a hydroxyl group and an amino group in the molecule, for example, ethanolamine.

Preferable examples of the low molecular weight diamine include ethylenediamine (hereinafter abbreviated to EDA), 1,2-propanediamine, 1,3-propanediamine, hexamethylenediamine, p-phenylenediamine, p-xylylenediamine, m-xylylenediamine, p,p☐-methylenedianiline, 1,3-cyclohexyldiamine, hexahydro-meta-phenylenediamine, 2-methylpentamethylenediamine, and bis(4-aminophenyl) phosphine oxide. EDA is particularly preferable. With the use of EDA, a resin having excellent elongation rate, elasticity, and heat resistance can be obtained. To such a chain extender, a triamine compound that can form a cross-linked structure, for example, diethylenetriamine and the like may be added to the extent that the chain extender does not lose its effect.

Preferable examples of the low molecular weight diol include ethylene glycol (hereinafter abbreviated to EG), 1,3-propanediol, 1,4-butanediol, bishydroxyethoxy benzene, bishydroxyethylene terephthalate, and 1-methyl-1,2-ethanediol. EG, 1,3-propanediol, and 1,4-butanediol are particularly preferable. With the use of these low molecular weight diols, the polyurethane resin can have heat resistance that is high for a diol-extended polyurethane. When the polyurethane resin is made into a polyurethane fiber, these low molecular weight diols contribute to high strength.

When the polyurethane resin is synthesized, it is also preferable to use a catalyst such as an amine catalyst and an organometallic catalyst either alone or in combination of two or more.

Examples of the amine catalyst include
N,N-dimethylcyclohexylamine, N,N-dimethylbenzylamine, triethylamine, N-methyl morpholine, N-ethyl morpholine, N,N,N',N'-tetramethylethylenediamine,
N,N,N',N'-tetramethyl-1,3-propanediamine,
N,N,N',N'-tetramethylhexanediamine, bis-2-dimethylamino ethyl ether, N,N,N',N',N'-pentamethyldiethylenetriamine, tetramethylguanidine, triethylenediamine,
N,N'-dimethylpiperazine,
N-methyl-N'-dimethylaminoethyl-piperazine,
N-(2-dimethylaminoethyl) morpholine, 1-methylimidazole, 1,2-dimethylimidazole, N,N-dimethylamino ethanol,
N,N,N'-trimethylaminoethyl ethanolamine,
N-methyl-N'-(2-hydroxyethyl) piperazine,
2,4,6-tris(dimethylaminomethyl) phenol,
N,N-dimethylaminohexanol, and triethanolamine.

Examples of the organometallic catalyst include tin octanoate, dibutyltin dilaurate, and dibutyl lead octanoate.

The method for synthesizing the polyurethane constituting the polyurethane resin of the present invention is not specifically limited, and a conventional method such as melt polymerization and solution polymerization can be used.

In the solution polymerization, the polyurethane can be synthesized using the ingredients mentioned above in a solvent of or a solvent composed primarily of, for example, N,N-dimethylacetamide (hereinafter abbreviated to DMAc), dimethylformamide (hereinafter abbreviated to DMF), dimethyl sulfoxide, N-methylpyrrolidone, and the like. Particularly preferable examples of the method include a so-called one-shot method, where each of the above-mentioned ingredients is put and dissolved in such a solvent, and heated up to a suitable temperature to react to give a polyurethane; and a method where a polymer diol and a diisocyanate are melted together, and the resulting reactant is dissolved in such a solvent and reacted with the chain extender mentioned above to give a polyurethane. In these methods, the concentration of the polyurethane solution to be obtained is generally preferably in the range of 30 to 80% by weight.

In the present invention, a capability of removing odor components such as nonenal, ammonia, acetic acid, and isovaleric acid is evaluated according to criteria of deodorant properties specified in the Certification Criteria of Deodorant-finished Textiles (updated on Sep. 1, 2007) established by Japan Textile Evaluation Technology Council (JTETC).

In the test for a capability of removing an odor, for example, an odor component and a sample are placed in a container and left for two hours, and then the residual concentration of the odor component is measured (the sample test concentration after two hours). The residual concentrations of nonenal and isovaleric acid are measured by gas chromatography, and the residual concentrations of ammonia and acetic acid are measured by a detector tube method. The blank test concentration in the following formula is the residual concentration in a container that contains the odor component alone. A decrease rate of the odor component is calculated from the following formula.

Decrease rate (%)=(blank test concentration after two hours−sample test concentration after two hours)/(blank test concentration after two hours)×100

When the decrease rate is as follows, it is determined that the sample has a capability of removing the odor component.

TABLE 1

| Odor component | Decrease rate |
| --- | --- |
| Nonenal | 75% or more |
| Ammonia | 70% or more |
| Acetic acid | 80% or more |
| Isovaleric acid | 85% or more |

There are cases where it is preferable to add various kinds of additives described below to the polyurethane resin used in the present invention. The various kinds of additives can be added by any kind of methods. Typical methods use a static mixer, a stirrer, a homomixer, a biaxial extruder, or the like. When a polyurethane is synthesized by solution polymerization, the various kinds of additives to be added are preferably brought into a solution and then added to the polyurethane in order to be added homogeneously.

Due to the addition of the various kinds of additives to the polyurethane solution, there are cases where the viscosity of the mixed solution becomes unexpectedly high compared with the viscosity of the polyurethane solution before the addition. In order to prevent the increase in the viscosity, it is also preferable to use an end-capping agent alone or in combination of two or more. Examples of the end-capping agent include monoamine such as dimethylamine, diisopropylamine, ethylmethylamine, diethylamine, methylpropylamine, isopropylmethylamine, diisopropylamine, butylmethylamine, isobutylmethylamine, isopentylmethylamine, dibutylamine, and diamylamine; monool such as ethanol, propanol, butanol, isopropanol, allyl alcohol, and cyclopentanol; and monoisocyanate such as phenyl isocyanate.

The polyurethane resin used in the present invention may contain various kinds of stabilizers, pigments, or the like if necessary as far as they do not reduce the effect of the present invention. Examples of such a stabilizer, pigment, or the like include a stabilizer such as an addition polymer of divinylbenzene and p-cresol ("Methacrol" (registered trademark) 2390 manufactured by DuPont), and a polyurethane obtained by reacting t-butyldiethanolamine and methylene-bis-(4-cyclohexyl isocyanate) ("Methacrol" (registered trademark) 2462 manufactured by DuPont); a light resistance agent, an antioxidant, and the like such as a both hindered phenol agent including so-called BHT, "Sumilizer" GA-80 manufactured by Sumitomo Chemical Co., Ltd., a benzotriazol agent and a benzophenone agent such as "Tinuvin" manufactured by Ciba-Geigy K.K., a phosphorus agent such as "Sumilizer" P-16 manufactured by Sumitomo Chemical Co., Ltd., various kinds of hindered amine agents; an inorganic pigment such as titanium oxide and carbon black; a fluorine resin powder; a silicone resin powder; a metallic soap such as magnesium stearate; a disinfectant and a deodorant agent containing silver, zinc, or a compound thereof; a lubricant such as silicone and a mineral oil; and various kinds of antistatic agents such as barium sulfate, cerium oxide, betaine, and a phosphoric acid-based antistatic agent. Such a stabilizer, pigment, or the like may be added to the polyurethane resin or reacted with a polymer of the polyurethane resin. In order to further increase durability especially against light, various kinds of nitrogen oxides, and the like, the following agent may be contained in the polyurethane resin: a nitrogen oxide scavenger such as HN-150 manufactured by Japan Hydrazine Co., Ltd.; a thermal oxidation stabilizer such as "Sumilizer" GA-80 manufactured by Sumitomo Chemical Co., Ltd.; and a light stabilizer such as "Sumisorb" 300#622 manufactured by Sumitomo Chemical Co., Ltd.

The glass transition point (Tg) of the polyurethane resin used in the present invention is one of indicators of its capability of removing an odor. When the polyurethane resin is used in an atmosphere having a higher temperature than Tg, the polyurethane resin exhibits an excellent permeability to a target gas and its capability of removing an odor increases accordingly, although the reason is unknown. That is, the deodorant material is preferably used in a temperature that is higher than Tg, and in order that the deodorant material should exhibit a high capability of removing an odor in actual use, the Tg is preferably $-100$ to $0°$ C.

Examples of a method for measuring the glass transition point (Tg) include a method with a viscoelastic modulus analyzer. For example, with the use of a dynamic elastic modulus analyzer RSA II manufactured by Rheometrics, Inc., the glass transition point (Tg) can be determined as loss tangent $\tan \delta = E''/E'$, which is calculated from temperature variances of a dynamic storage elastic modulus $E'$ and a dynamic loss elastic modulus $E''$ at a temperature increase rate of $10°$ C./minute.

In view of obtaining a material that is free from practical problems including problems in the production process and at the same time excels in high heat resistance, the polyurethane resin used in the present invention particularly preferably comprises a product obtained by reacting a polymer diol and a diisocyanate and has its higher melting point in the range of 150 to $300°$ C. The higher melting point refers to a melting point of a so-called hard segment crystal of a polyurethane or a polyurethane urea measured with a differential scanning calorimeter (DSC).

Examples of a method for adjusting the Tg of a polyurethane or a polyurethane urea to a range of $-100$ to $0°$ C. and at the same time adjusting the higher melting point to a range of 150 to $300°$ C. include a method for adjusting the ratio of a polymer diol and a diisocyanate. For example, when the number average molecular weight of the polymer diol is 1000 or more, a polyurethane whose Tg is $-100°$ C. or more and whose higher melting point is $150°$ C. or more can be obtain by polymerization at the ratio of (the mole number of a diisocyanate)/(the mole number of a polymer diol)=1.5 or more.

In view of increasing the capability of removing an odor, the concentration of urethane group in a polyurethane constituting the polyurethane resin used in the present invention is preferably about 0.2 to 3.5 mol/kg, more preferably about 0.4 to 1.0 mol/kg. The concentration of urethane group is calculated by the following formula: (the amount of a polymer diol (mol) in a polyurethane resin)×2/(the weight of a polyurethane resin (kg)).

The concentration of effective terminal amine in a polyurethane constituting the polyurethane resin used in the present invention is preferably 15 to 50 meq/kg. The concentration of the effective terminal amine is calculated by the following method. First, a solution of a polyurethane or a polyurethane urea is diluted with DMAc to give 25 ml of a solution having a concentration of 2% by weight. The solution is subjected to potentiometric titration with p-toluenesulfonic acid (0.01N) to determine (a) the sum concentration of primary amine and secondary amine. Next, salicylaldehyde is added to the solution to react with the primary amine. After that, potentiometric titration of the secondary amine with p-toluenesulfonic acid (0.01N) is carried out to determine (b) the concentration of the secondary amine. The concentration of the effective terminal amine is calculated by the following formula.

$$\text{Concentration of effective terminal amine (meq/kg)} = (a)-(b)$$

Examples of a preferable form of the polyurethane resin used in the present invention include a fiber, a film, a resin-molded product (a sheet, a stick body, a tube body, a molded product in variant forms, a foam body thereof, and the like), a compression-molded product of microparticles, and an impregnated material. Among these, a fiber is most preferable. The polyurethane resin formed into a fiber can be easily mixed with other kinds of materials and can be made into various kinds of fabrics or fiber structures.

When the polyurethane resin used in the present invention is used in the form of a fiber, the fiber is preferably a polyurethane fiber that comprises as a polymer diol, a polyalkylene ether diol comprising 5 to 25 mole of the following structural unit (a) and 95 to 75 mobs of the following structural unit (b) and having a number average molecular weight of 250 to 10000; a diisocyanate compound; and a chain extender. The polyurethane fiber is particularly preferably made from a polyurethane urea polymerized with the use of, as the chain extender, a diamino compound (low molecular weight diamine). The polyurethane fiber is obtained by a usual spinning method.

Formula 3

Structural unit (a):

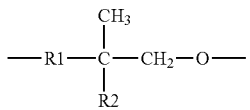

Structural unit (b):

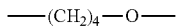

(wherein R1 represents a straight-chain alkylene group having 1 to 3 carbon atoms, and R2 represents hydrogen or an alkyl group having 1 to 3 carbon atoms)

The structural unit (a) mentioned above is obtained by introducing a side chain into a polyalkylene ether diol, and exemplified by a structural unit derived from 3-methyl-tetrahydrofuran, or a structural unit derived from neopentyl glycol. Among these, a structural unit expressed by the above-mentioned formula having R1 representing a straight-chain alkylene group having 2 carbon atoms and R2 representing hydrogen is particularly preferable.

The polyurethane fiber obtained by introducing a side chain into a molecular chain of a polyalkylene ether diol as mentioned above has high flexibility, high resilience, and a low Tg; thus the fiber can exhibit a higher capability of removing an odor. The fiber furthermore has an improved durability against high temperature dyeing or high temperature thermosetting, and thus remarkably controls decrease in its recovery stress.

A copolymer comprising the structural unit (a) and the structural unit (b) is preferably obtained by block copolymerization or random copolymerization. In the copolymer obtained by random copolymerization, more structural units (a) preferably exist at the end of the molecular chain. That is, it is preferable that the ratio of the structural unit (a) to positions neighboring an OH group of the molecular chain (the ratio of terminal (a)) be more than the ratio of the structural unit (a) to the molecular chain (the ratio of total (a)). For example, the ratio of terminal (a) is preferably twice or more as high as the ratio of total (a). This ratio can increase a retention rate of recovery stress of a polyurethane fiber, especially when the polyurethane fiber dyed at a high temperature is a polyurethane elastic fiber.

In order to make more structural units (a) exist at the end of the molecular chain as mentioned above, at the end of a process for polymerizing a monomer forming the structural unit (a) and a monomer forming the structural unit (b), the monomer forming the structural unit (a) has to be additionally supplied and reacted. By controlling the amount of the monomer additionally supplied, the timing of the supply, or the like, the ratio of the structural unit (a) existing at a position neighboring an OH group of the molecular chain can be adjusted to a desired level.

With the use of 3-methyl-tetrahydrofuran and tetrahydrofuran as each of the monomers mentioned above, a polyalkylene ether diol comprising the structural unit (a) and the structural unit (b) can be produced by copolymerization at a temperature of about 0 to 50° C. in the presence of a catalyst such as chlorosulfonic acid, 2-fluorosulfonic acid, and perchloric acid, all of which are strong acids that can open the ring of the tetrahydrofuran.

The ratio of total structural unit (a) is 5 to 25 mol %, preferably 8 to 20 mol % of the polyalkylene ether diol. The structural unit (b) accounts for the remaining ratio. With the structural unit (a) in such a ratio, dyeing at a high temperature can be more preferably carried out.

The number average molecular weight of the polymer diol used in the present invention is preferably 1000 to 8000, more preferably 1800 to 6000, because when the polymer diol is made into a polyurethane fiber, the fiber should have a desired level of a capability of removing an odor, elongation rate, strength, heat resistance, and the like. With the use of the polymer diol having a molecular weight in such a range, a polyurethane fiber or a polyurethane elastic fiber that excels in elongation rate, strength, elastic resilience, heat resistance, and a capability of removing an odor can be obtained.

Since a polyurethane fiber preferably used in the present invention comprises a polyurethane or a polyurethane urea obtained by polymerization with the use of the particular polyalkylene ether diol mentioned above as a polymer diol, the polyurethane fiber is a polyurethane elastic fiber having high elongation rate and strength. Furthermore, the polyurethane elastic fiber can be dyed several times, and even after being dyed, the fiber can retain high stretchiness.

As a diisocyanate compound to be reacted with the polymer diol, a usual diisocyanate compound, for example, MDI is used.

Examples of a preferable diamino compound (low molecular weight diamine) constituting the polyurethane fiber used in the present invention include a symmetric diamino compound such as ethylenediamine, diaminodiphenylmethane, and p-phenylenediamine, but in view of a capability of removing an odor, EDA is preferable.

A polyurethane fiber produced from the polyurethane described below is preferable, because the polyurethane fiber has an especially high elongation rate and a high capability of removing an odor, and further is free from practical problems including problems in the production process as mentioned above, and at the same time has an excellent high heat resistance: the polyurethane having a Tg of −100 to 0° C. and its high melting point of 150 to 300° C. is synthesized using, as a polymer diol, PTMG or modified PTMG having a number average molecular weight of 1000 to 8000, preferably 1800 to 6000; as a diisocyanate, MDI; and as a chain extender, at least one selected from the group consisting of EG, 1,3-propanediol, 1,4-butanediol, EDA, 1,2-propanediamine, and 1,3-propanediamine.

In a process for producing a polyurethane fiber that is preferably used in the present invention, a method for producing a polyurethane solution or a polyurethane, which is a solute of the polyurethane solution, may be either melt polymerization or solution polymerization, or any other method. However, solution polymerization is more preferable. When solution polymerization is employed, it is easy to spin the polyurethane and to produce a polyurethane fiber having low fineness since the polyurethane has rare occurrences of an unfavorable substance such as a gel. Solution polymerization also has an advantage of omitting a step of the conversion into a solution.

The polyurethane fiber can be synthesized using the ingredients mentioned above in a solvent of, for example, DMAc, DMF, dimethyl sulfoxide, N-methylpyrrolidone, and the like, or in a solvent containing these as a chief ingredient. Particularly preferable examples of the method include a so-called one-shot method, where each of the above-mentioned ingredients is put and dissolved in such a solvent, and heated up to a suitable temperature to react to give a polyurethane; and a method where a polymer diol and a diisocyanate are melted together, and the resulting reactant is dissolved in such a solvent and reacted with the chain extender mentioned above to give a polyurethane. In these methods, the concentration of the polyurethane solution to be obtained is generally preferably in the range of 30 to 80% by weight.

With the use of, among such a polyurethane fiber, a polyurethane urea elastic fiber having high elongation rate with the following spun yarn containing a carboxyl group if necessary, a stretch fabric having high stretchiness as a preferable embodiment of the present invention can be obtained.

The polyurethane elastic fiber mentioned above, as the polyurethane resin, further preferably has a retention rate of recovery stress where the fiber is elongated to 100% in steam of 130° C. for 1 minute (a retention rate compared with the recovery stress of a yarn that is not exposed to the steam, hereinafter, referred to as a retention rate after steam exposure) of 85% or more, more preferably 90% or more. When a fabric, as a stretchy fiber structure, is produced with the use of the polyurethane elastic fiber having such a retention rate after exposure of steam together with a spun yarn containing a carboxyl group, a stretch fabric having few problems in high temperature dyeing or repeated dyeing can be obtained.

It is more preferable to use a polyurethane urea elastic fiber preferably having a retention rate of recovery stress where the fiber is elongated to 100% in hot air of 200° C. for 1 minute (a retention rate compared with the recovery stress of a yarn that is not exposed to the hot air, hereinafter, referred to as a retention rate after dry heat exposure) of 50% or more, more preferably 55% or more. Even when the polyurethane urea elastic fiber, as a material that gives stretchiness, is mixed with a fabric comprising a spun yarn containing a carboxyl group, which, requires high temperature thermosetting in dyeing and finishing, the mixed fabric can undergo thermosetting without any problems, and thus a good stretch fabric can be obtained.

The polyurethane urea elastic fiber preferably used in the present invention comprises the particular polyurethane urea mentioned above, and further preferably have the properties mentioned above. The process for producing the polyurethane urea elastic fiber having the properties is not specifically limited, and the polyurethane urea elastic fiber can be produced by suitably adjusting a constitution and molecular weight of a polyurethane urea, a spinning condition, and the like.

Next, a deodorant material of the present invention also preferably contains a fiber containing a carboxyl group, and more preferably contains a cellulose fiber containing a carboxyl group.

This will be explained below.

The concentration of carboxyl group in a fiber containing a carboxyl group is preferably 30 to 3000 meq/kg. The concentration of carboxyl group is determined by diluting a solution of the fiber containing a carboxyl group (The solvent is a mixed solvent of DMAc and acetone, or a DMAc solution containing lithium chloride, and the like.) to give 25 ml of a solution having a concentration of 2% by weight, and then titrating with the use of a 0.01N sodium hydroxide/benzyl alcohol solution.

The preferable embodiment of the fiber containing a carboxyl group used in the present invention is a spun yarn (A) comprising 100 to 5% by weight of a cellulose fiber containing a carboxyl group and 0 to 95% by weight of a polyester fiber.

Examples of the cellulose fiber include a natural cellulose fiber such as cotton and hemp, a regenerated cellulose fiber such as rayon, a semi-synthetic cellulose fiber, and a so-called non-designated fiber (lyocell, cuprammonium rayon). Lyocell is especially preferably used for producing a deodorant material of the present invention as a clothing material due to its soft texture and good moisture absorbency.

The cellulose fiber containing a carboxyl group comprises a modified cellulose fiber obtained by graft-copolymerizing the cellulose fiber mentioned above with methacrylic acid. The modified cellulose fiber has an excellent capability of adsorbing a malodorous basic substance such as ammonia, amine, a urine odor, and serves as a deodorant fiber. The production method of the modified cellulose fiber is disclosed in JA Patent No. 3239146 (JP-A-6-184941). For example, the method is radiation-induced graft polymerization onto a textile under the condition that the textile is immersed in a methanol solution containing either a monomer mixture comprising acrylic acid and sodium vinyl sulfonate or a hydrophilic vinyl monomer mixture comprising acrylic acid and vinylbenzyl trimethylammonium chloride.

The weight of the cellulose fiber graft-polymerized with the hydrophilic vinyl monomer preferably increases by 2 to 30% by weight (the graft rate is 2 to 30% by weight), compared with the weight thereof measured before the graft polymerization, and the graft rate is more preferably 5 to 15% by weight.

The above-mentioned fiber containing a carboxyl group is also preferably mixed-spun with a polyester fiber, and used as a spun yarn.

The polyester fiber is not specifically limited, but is a polyester fiber obtained from a polyester resin that is obtained by copolymerizing mainly polyethylene terephthalate, polybutylene terephthalate, polyethylene terephthalate, polytetramethylene glycol terephthalate, or the structural unit thereof, together with other components. An especially preferable polyester fiber is a polyethylene terephthalate fiber, i.e., a fiber containing, as a main polymer, polyethylene terephthalate or copolymerized polyethylene terephthalate.

Preferable examples of the polyethylene terephthalate fiber to be used include a fiber comprising a main repeating unit of polyethylene terephthalate, polybutylene terephthalate, or ethylene terephthalate (of specifically 90 mol % or more of repeating units), or a main repeating unit of butylene terephthalate (of specifically 90 mol % or more of repeating units). Among these, the fiber especially preferably comprises a polyester comprising 90 mol % or more of a repeating unit of ethylene terephthalate, and the fiber more preferably comprises a polyester comprising 95 mol % or more of a repeating unit of ethylene terephthalate. The fiber further preferably comprises a polyester comprising 100 mol % of a repeating unit of ethylene terephthalate (namely, polyethylene terephthalate). This polyethylene terephthalate fiber has a good texture and luster, and the fiber is easy to care for since the fiber has crease-resistance and the like; therefore the fiber is suitable for a fiber material constituting a fabric having stretchiness. The polyethylene terephthalate fiber is preferable when used with a polyurethane urea elastic yarn that is preferably used in the present invention, and the polyethylene terephthalate fiber can be formed into a fabric having a good stretchiness.

The cross section of these polyester fibers may be in any shape such as a circular shape and a modified shape.

It is preferable to use a polyester fiber yarn having moisture-absorbing and quick-drying properties. Examples of a synthetic fiber having moisture-absorbing and quick-drying properties include a hollow fiber having many further small holes on its wall; and a modified cross-section fiber having many grooves, holes and the like on the fiber surface and the like in order that moisture is absorbed in the minute holes, the grooves, a space between the fibers, and a space between the yarns. As the synthetic fiber having moisture-absorbing and quick-drying properties, various kinds of products marketed as a synthetic fiber having moisture-absorbing and quick-drying properties from synthetic fiber manufacturers can be used. Examples of the polyester fiber having moisture-absorbing and quick-drying properties include "COOLMAX" manufactured by INVISTA SARL, "CEOα" manufactured by Toray Industries, Inc., "WELLKEY" manufactured by Teijin Fibers, Ltd., "DRY FAST" manufactured by Toyobo Co., Ltd., and "TECHNOFINE" manufactured Asahi Kasei Corporation.

Fibers provided with moisture-absorbing and quick-drying properties include fibers provided with minute holes or spaces into which moisture penetrates, for example, as mentioned above, a hollow fiber that is made from a polymer material with low moisture absorbency, such as a polyester fiber and an acrylic fiber, and is provided with many further small holes on its wall; and a modified cross-section fiber having many grooves, holes and the like on the fiber surface and the like in order that moisture is absorbed in the minute holes, the grooves, a space between the fibers, and a space between the yarns.

As a synthetic fiber having antistatic properties, a polyester conductive fiber may be used if necessary. Examples of the conductive fiber include a composite polyester fiber containing a conductive substance such as carbon black (for example, "Belitron" manufactured by KB SEIREN CO., LTD.), and a composite polyester fiber containing white copper iodide or a metal composite oxide (for example, $TiO_2.SnO_2.Sb_2O_2$), but are not limited thereto.

The polyester fiber used in the present invention preferably has a fiber surface area of $0.1 \text{ m}^2$ or more per gram of a woven or knitted fabric, or a single fiber fineness of about 3 deniers or less, more preferably a surface area of $0.12 \text{ m}^2$ or more, or a single fiber fineness of about 3 deniers or less. Since the attachment of an antimicrobial agent to a fiber or the exhaustion of an antimicrobial agent by a fiber depends on the surface area of the fiber or the single fiber fineness of the fiber, a fiber having a surface area of $0.1 \text{ m}^2$ or more, or a single fiber fineness of about 3 deniers or less can give an antimicrobial fiber structure (fabric) having a high durability against industrial laundry.

The above-mentioned spun yarn (A) comprising a cellulose fiber containing a carboxyl group and a polyester fiber comprises, relative to 100% by weight of the spun yarn, 100 to 5% by weight of the cellulose fiber containing a carboxyl group and 0 to 95% by weight of the polyester fiber.

The content ratio of the cellulose fiber containing a carboxyl group in the spun yarn is 100 to 5% by weight, preferably 100 to 10% by weight, more preferably 100 to 50% by weight, especially preferably 75 to 60% by weight. By using an unmodified cellulose fiber with the cellulose fiber containing a carboxyl group, the content ratio of the cellulose fiber containing a carboxyl group in the spun yarn can be adjusted to the preferable content ratio mentioned above. When the content ratio of the cellulose fiber containing a carboxyl group is 5% by weight or less, the effect of removing an odor is extremely low.

The spun yarn (A) also preferably comprises 0 to 95% by weight of a polyester fiber.

The spun yarn (A) may comprise 100 to 5% by weight of a cellulose fiber containing a carboxyl group and 0 to 95% by weight of a polyester fiber, and further comprise less than 50% by weight of one or more kinds of natural fibers such as wool and silk or synthetic fibers, except polyester fibers.

In view of increasing moisture absorbency, the spun yarn (A) is preferably a blended yarn of a cellulose fiber containing a carboxyl group (preferably a modified lyocell fiber) and a polyester fiber, especially preferably a blended yarn of a cellulose fiber containing a carboxyl group and a polyester fiber having moisture-absorbing and quick-drying properties, or preferably a blended yarn of a cellulose fiber containing a carboxyl group and a polyester conductive fiber having antistatic properties.

The spun yarn may be produced according to a known method, and the spun yarn is preferably produced by one or more production methods selected from, for example, ring traveler spinning, open end spinning, binding spinning, and twist spinning. The fineness of the spun yarn (A) is not specifically limited, but preferably 6 to 60 English yarn count. A yarn count refers to a unit of the thickness of a yarn, and a bigger yarn count means a thinner yarn. Either a single yarn or a two ply yarn having the thickness in the range mentioned above can be preferably used in the present invention.

A yarn thicker than a 6-count yarn is not preferable since a base fabric made of the yarn is too thick and lacks softness, and a yarn thinner than a 60-count yarn is also not preferable since a fabric made of the yarn is too thin and easily damaged.

A deodorant material of the present invention comprises, for example, either a polyurethane fiber or a polyurethane urea fiber, a fiber containing a carboxyl group, and further, if desired, a polyester fiber and the like. Preferable embodiments of the deodorant material include a stretch fabric as mentioned above.

A stretch fabric, which is a preferable embodiment of the present invention, may suitably contain various kinds of inorganic or organic additives, stabilizers, antimicrobial agents, or the like. Examples of the additives or agents include various kinds of minerals such as a hydrotalcite compound, huntite, hydromagnesite, and tourmaline; an oxide, a composite oxide, and a hydroxide of a metal such as Ca, Mg, Zn, Al, Ba, and Ti. Such an additive or agent may be contained as far as it does not reduce the effect of the present invention When such an inorganic additive is mixed in a fiber, in view of increasing dispersibility of the inorganic additive in the fiber and stabilizing spinning operation, it is also preferable to use an inorganic agent whose surface is treated with, for example, an organic substance such as a fatty acid, a fatty acid ester, and a polyol-based organic substance; or a silane-based coupling agent, a titanate-based coupling agent, or a mixture thereof.

The stretch fabric mentioned above also preferably has an antimicrobial finish with an antimicrobial agent. The antimicrobial agent has most excellent antimicrobial performance when attached to the surface of a fiber because the antimicrobial agent is in frequent contact with bacteria. However, the antimicrobial agent on the surface of a fiber has low washing durability because it easily peels off; therefore the attachment of the antimicrobial agent to the surface of a fiber is not preferable. On the other hand, when the antimicrobial agent is uniformly dispersed inside a fiber, the antimicrobial performance decreases but washing durability increases. From the facts mentioned above, it is considered that the antimicrobial agent has most excellent antimicrobial performance and washing durability when the antimicrobial agent is annularly distributed internally close to the surface of a fiber, or when the antimicrobial agent is dispersed so as to be diverged from the fiber surface toward the inside of the fiber.

Examples of the antimicrobial agent include various kinds of organic and inorganic compounds. The antimicrobial agent is preferably one or more selected from an organic nitrogen-sulfur compound, a quaternary ammonium compound, a phosphoric ester compound, and an inorganic compound containing a metal ion.

Examples of the organic antimicrobial agent include an organic nitrogen-sulfur compound; a phenol compound; an organic antimicrobial agent having an antimicrobial metal ion such as an organotin compound, an organocopper compound, and an organosilver compound; various kinds of organosilicone quaternary ammonium salts; a quaternary ammonium salt of an alkyl phosphoric acid ester (for example, cetyl dimethyl ammonium chloride); an organic antimicrobial agent such as benzalkonium chloride, alkyl aryl sulfonate, halo phenol, and mercuric phenyl acetate; polyphenols; and chitosan.

The antimicrobial active site of the antimicrobial agent is preferably an amino group, more preferably an allyl amino group and a diaryl amino group, in particular, preferably a condensate of dimethylamine and epichlorohydrin, a diarylamine derivative-based polymer, and a polymer of allylamine and a vinylamine derivative. Primary, secondary, and tertiary allylamine-based polymers are preferable in view of washing durability, and with the use of such a polymer, a higher effect of removing an odor can be achieved without impairing the softness of a fabric.

The antimicrobial finish with the organic antimicrobial agent can be generally obtained by a continuous method where a material is continuously padded, dried, and cured with the use of the antimicrobial agent in aftertreatment, or by a batch processing where a material is heated and processed with a jet dyeing machine and the like. It is also possible to use a fiber already containing the antimicrobial agent as a structural fiber, and in this case it is preferable to make the fiber containing the antimicrobial agent exposed on the surface of a fabric material. The batch processing is preferable in view of uniformly providing a capability of removing an odor and washing durability.

The inorganic antimicrobial agent is not specifically limited, and examples of the inorganic antimicrobial agent include a hydroxide of a transition metal such as copper, silver, zinc, titanium, zirconium, vanadium, molybdenum, tungsten, chromium, iron, cobalt, nickel, manganese, germanium, and cerium; a hydroxide of an amphoteric metal such as aluminum, silicon, tin, and antimony; a hydroxide of magnesium, and the like; and a carbonate, a phosphate, a silicate, an aluminate, and a zirconate of a metal except an alkaline metal. Among these metallic compounds, zinc hydroxide and basic zinc carbonate are especially preferable.

It is also possible to use an antimicrobial material obtained by a method where a fabric is immersed in a dispersion solution where a microparticle of zeolite supporting silver is dispersed in a binder, and the fabric is dried and cut into a predetermined size. As a carrier of the silver, besides zeolite, hydroxyapatite, silica gel, silica-alumina, zirconium phosphate, and the like can also be used.

Instead of using the silver supported by zeolite, it is also preferable to immerse a fabric in a solution containing one or more selected from the following antimicrobial agents, or to attach a carrier supporting one or more selected from the following antimicrobial agents with the use of a binder: an antimicrobial metal such as copper and zinc, an oxide thereof, a hydroxide thereof, or a salt thereof; β-thujaplicin (hinokitiol); polyphenons; a tea tree oil; a cationic surfactant such as a benzalkonium chloride surfactant and a benzethonium chloride surfactant; an amphoteric surfactant such as alkylpolyamino ethylglycine hydrochloride; a biguanide compound such as chlorhexidine gluconate and polyhexamethylene biguanidine hydrochloride; 2-(4-thiazolyl) benzimidazole; N-(fluorodichloromethylthio) phthalimide; 2,3,5,6-tetrachloro-4-(methylsulfonyl)-pyridine; 10,10'-oxybisphenoxyarsine; trimethoxysilyl-propyl octadecyl ammonium chloride; 2-n-octyl-4-isothiazolin-3-one; bis (2-pyridylthio-1-oxide) zinc; sodium dehydroacetate; salicylic acid; p-hydroxybenzoate esters; N-cocoyl-L-arginine ethyl ester.pyrrolidone carboxylic acid salt; and hexachlorophene.

Inter alia, zinc oxide in the form of microparticles can exhibit a capability of removing an odor and of inhibiting the growth of bacteria, as well as a high capability of chemically removing a body odor, i.e., an acid gas originating from the decomposition of sweat, for example, acetic acid, isovaleric acid, and the like. It is proved that zinc oxide is highly safe for a human body, so that zinc oxide is used for an ingredient of cosmetics. Zinc oxide therefore excels as an antimicrobial agent for clothes, which are directly in contact with skin, and as an agent for removing the acid gas.

It is also preferable to use an antimicrobial agent comprises an optical semiconductor powder, whose photocatalytic effect destroys or inhibits the growth of bacteria. The photocatalytic effect is brought about as a chemical reaction in an electrochemical cell where one electrode is an optical semiconductor ceramic, which is the optical semiconductor powder, and the other electrode is a metal. Examples of the optical semiconductor powder used include $TiO_2$, CdS, CdSe, $WO_3$, $Fe_2O_3$, $SrTiO_3$, and $KNbO_3$. Examples of the metal powder used include various kinds of metal powders of, for example, gold, silver, platinum, and copper.

The amount of the above-mentioned antimicrobial agent used in a deodorant material of the present invention is preferably about 0.1 to 10% by weight, especially preferably about 0.1 to 5% by weight, and the antimicrobial agent is preferably exhausted by or loaded on the deodorant material.

A stretch fabric, which is a preferable embodiment of the present invention, preferably exhausts or is loaded with the antimicrobial agent in a treatment solution having a pH of 5.0 to 6.0.

That is, a treatment where the antimicrobial agent is exhausted by or loaded on a stretch fabric comprising 99 to 70% by weight of the spun yarn (A) and 1 to 30% by weight of a polyurethane elastic fiber (B) is generally carried out by a conventional method such as dipping of the fabric in a treatment solution where the antimicrobial agent is, if necessary, dissolved in a solvent. The pH of the treatment solution in this treatment is preferably in the range of 5.0 to 6.0, and at the pH in this range, a specified amount of the antimicrobial agent uniformly infiltrates the fabric, and the antimicrobial agent is exhausted by the fabric. The treatment time is preferably 1 to 120 minutes, and the treatment temperature is preferably 40 to 200° C.

A treatment where the antimicrobial agent is exhausted by or loaded on the fabric is generally carried out by a conventional method, including, for example, a batch processing or a continuous processing where the treatment is carried out simultaneously with dyeing in a stain solution containing the antimicrobial agent. In cases where only a treatment where the antimicrobial agent is exhausted by or loaded on the fabric is carried out, examples of the treatment include immersing or dipping of the fabric or a textile containing the fabric in a treatment solution where the antimicrobial agent is, if necessary, dissolved and dispersed in a solvent (for example, water or an organic solvent such as methanol). The batch processing is preferable in view of uniformly providing a capability of removing an odor and washing durability. The treatment solution in these cases preferably maintains acidity in order to protect the carboxyl group contained in the fabric and thereby exhibit an excellent capability of removing an odor. Examples of a preferable pH of the treatment solution containing the antimicrobial agent include 5.0 to 6.0, and at the pH in this range, a specified amount of the antimicrobial agent is uniformly absorbed by the fabric and the antimicrobial agent can be exhausted by or loaded on the fabric. In a process where the treatment is carried out simultaneously with dyeing in a fabric stain solution containing the antimicrobial agent, when the fabric is dyed in a dark color such as black and dark blue, the pH is preferably 5.0 to 6.0 so that the fabric can produce a great color, and when the fabric is dyed in white or a pale color, the pH is preferably 5.3 to 6.0 so that the fabric can exhibit a capability of removing an odor and the fabric does not turn yellow. The process time of the exhaustion or dipping is generally preferably about 1 to 120 minutes.

A material having a high capability of adsorbing an odor component such as ammonia, methyl mercaptan, and hydrogen sulfide may be further added or adhered to the surface of the fiber if necessary. Examples of the material (the deodorant agent) include activated charcoal, silica gel, alumina, activated clay, molecular sieve, and amorphous aluminosilicate having a high bulk specific gravity. Of course, a fiber already containing the deodorant agent may be used.

Examples of the deodorant agent include a ceramic powder such as zeolite, apatite, activated charcoal, activated alumina, activated silica gel, bentonite, and sepiolite; a material containing a silk fiber; a metal salt of iron, copper, and the like; and a mixture thereof. Since these deodorant agents have functions of not only removing an odor but also absorbing moisture, one kind of these deodorant agents alone can provide the fabric with both functions of removing an odor and absorbing moisture. Among these, zeolite is especially preferable. Zeolite has properties of an amorphous or beehive structure having innumerable micropores and of a big specific surface area. Because of these properties, when zeolite is in contact with humidity, the micropores of zeolite absorb moisture and simultaneously further absorb not only an inorganic gas containing four major foul odor (ammonia, trimethylamine, hydrogen sulfide, and methyl mercaptan) but also an organic gas containing isovaleric acid, phenol, and the like.

A stretch fabric, which is a preferable embodiment of the present invention, can be obtained by a conventional method with the use of the above-mentioned polyurethane resin, or the above-mentioned polyurethane resin and the above-mentioned fiber containing a carboxyl group, and further a polyester fiber if desired. The stretch fabric may be any of a woven fabric, a knitted fabric, and a nonwoven fabric. For example, the stretch fabric may be made of a covered yarn obtained by covering a polyurethane elastic fiber with the spun yarn (A) containing a carboxyl group, or the stretch fabric may be a mixed woven or knitted fabric obtained by weaving or knitting a polyurethane elastic fiber as a naked yarn (bare yarn) with the spun yarn (A).

In cases where the stretch fabric is a woven fabric, the stretch fabric may also be woven only from a fiber comprising a polyurethane resin, or mixed-woven from different kinds of fibers.

Preferable examples of weave of the woven fabric include three basic weave such as plain weave, twill weave, and satean weave; derivative weave such as derivative plain, weave, derivative twill weave, and derivative satean weave; special weave such as honey-comb weave, mock leno weave, and crepe weave; single-backed double weave such as warp backed weave and weft backed weave; double weave such as reversible figured, hollow weave, and double velvet; multi-ply weave such as belt weave; warp pile weave such as warp velvet, towel cloth, seal skin cloth, and velour; weft pile weave such as velveteen, weft velvet, velvet, and corduroy; and leno weave such leno, plain gauze, and brocade gauze.

Weaving is preferably carried out with a shuttle loom (a flying shuttle loom, and the like) or a shuttleless loom (a rapier loom, a gripper loom, a water jet loom, an air jet loom, and the like), or the like.

In cases where the stretch fabric is a knitted fabric, the stretch fabric may also be knitted only form a fiber comprising a polyurethane resin, or mixed-knitted from different kinds of fibers. The knitted fabric may be a weft knitted fabric, a warp knitted fabric, or the like. Preferable examples of stitch of the weft knitted fabric include plain stitch, rib stitch, interlock stitch, purl stitch, tuck stitch, float stitch, half cardigan stitch, lace stitch, and pile stitch. Preferable examples of stitch of the warp knitted fabric include single denbigh stitch, single atlas stitch, double cord stitch, half tricot stitch, fleecy stitch, and jacquard stitch. The knitted fabric may be a single-ply knitted fabric or a multi-ply knitted fabric containing two or more plies.

Knitting is preferably carried out with a flat knitting machine such as a circular knitting machine, a weft knitting machine, and a Cotton knitting machine; a tricot knitting machine; a Raschel knitting machine; or a Milanese knitting machine; or the like.

A fabric of the present invention is especially suitable for hosiery such as tights, stockings, panty hoses, and socks; and underwear.

As a deodorant material having a capability of removing the odor of nonenal, ammonia, acetic acid, and isovaleric acid, for example, the above-mentioned stretch fabric comprising a polyurethane fiber and a fiber containing a carboxyl group is preferable.

A stretch fabric, which is a preferable embodiment of the present invention, comprises 99 to 70% by weight of the spun yarn mentioned above and 1 to 30% by weight of a polyurethane elastic fiber, preferably 95 to 80% by weight of the spun yarn and 5 to 20% by weight of a polyurethane elastic fiber.

The fineness of the polyurethane elastic fiber is not specifically limited, and suitably selected according to a use.

A stretch fabric, which is a preferable embodiment of the present invention, preferably has a fabric weight of 100 to 1000 g/m$^2$ and an elongation rate in the longitudinal direction and/or lateral direction of 5% or more, especially preferably has a fabric weight of 150 to 280 g/m$^2$.

Examples of a principal use of the deodorant material of the present invention include clothes (underwear, intermediate wear, outerwear, swimwear, and a hygiene material such as a disposable diaper), towel cloth, socks, a supporter, a food packaging material, a carpet, an interior material, a car seat cover, bedding, a building material, a wall material, and a filter material, but not limited thereto.

It is also preferable to use a polyurethane resin for producing a deodorant material for removing the odor of nonenal.

EXAMPLE

The present invention will be described more specifically with the reference to the following Examples and Comparative Examples, but the present invention is not limited thereto. Hereinafter "%" means "% by weight."

<Odor Removal Test on Nonenal>

An odor removal test was carried out with the use of, as an odor component, 2-nonenal ($C_9H_{16}O_{10}$, molecular weight: 140.2, CAS number: 463-53-8, hereinafter simply referred to as nonenal), which is a cause of a distinctive body odor of the middle-aged and elderly, and a capability of removing the odor was evaluated by the following method.

The instrumental analysis thereof was carried by gas chromatography. When a decrease rate of nonenal was 75% or more, it was determined a sample passed the test (represented by "good").

Example 1

As a polyalkylene ether diol, a copolymerized tetramethylene ether diol having a number average molecular weight of 2500 (containing 12.5 mol % of a structural unit (a) derived from 3-methyl-tetrahydrofuran) obtained by the following copolymerization process was used: 87.5 mol of dehydrated tetrahydrofuran and 12.5 mol of dehydrated 3-methyl-tetrahydrofuran were placed in a reactor equipped with a stirrer, and a polymerization reaction was carried out in the presence of a catalyst (a mixture of 70% by weight of perchloric acid and 30% by weight of acetic anhydrides) under a nitrogen seal at a temperature of 10° C. for 8 hours. After the reaction, the resultant product was neutralized with a sodium hydroxide solution to give the copolymer.

The copolymerized tetramethylene ether diol and 4,4'-MDI were placed in a container so that the amount of 4,4'-MDI relative to 1 mol of the tetramethylene ether diol was 1.97 mol, and the mixture was reacted at 90° C. The obtained product was dissolved in N,N-dimethylacetamide (DMAc) with good stirring to give a solution. Next, to the solution containing the dissolved product, a DMAc solution containing, as a chain extender, 60 mol % of ethylenediamine (EDA) and 40 mol % of 1,2-propanediamine (1,2-PDA) was added. To this solution, a DMAc solution containing, as an end-capping agent, diethylamine was further added to give a polyurethane urea solution having a polymer solid content of 25% by weight. The obtained solution at 40° C. had a viscosity of about 2400 poise. The limiting viscosity of the polymer measured in a 0.5 g/100 ml solution of DMAc at 25° C. was 0.95.

The polyurethane urea solution was extruded from a spinneret into an inert gas (a nitrogen gas) having a high temperature (350° C.) to give four filaments. The filaments were dried as passing through the high temperature gas. Before being completely dried, the filaments were led through an air jet twister so that the four filaments were twisted and coalesced. The resultant fiber was rolled up at a rate of 540 m/minute. From the coalesced four filaments, a polyurethane urea fiber having a dtex of 44 (B-a) was produced. (B-a) had a glass transition point (Tg) of −70° C. The concentration of urethane group in a polyurethane urea constituting the polyurethane urea fiber (B-a) was 0.49 mol/kg and the concentration of effective terminal amine was 28 meq/kg.

Only (B-a) was fed into a single cylinder knitting machine having 320 needles and a cylinder diameter of 3.5 inches (29 gauges), knitted, and steam-set at 120° C. for 1 minute to give a cylindrically knitted fabric having a width of about 5 cm (55 g/m$^2$). The obtained fabric was used as a sample without opening its width (The fabric is equivalent to two plies of a knitted fabric of 55 g/m$^2$.), and an odor removal test on nonenal was carried out. The result is shown in Table 2.

The decrease rate of nonenal in the odor removal test was 80%.

Example 2

The copolymerized tetramethylene ether diol obtained in Example 1 and 4,4'-MDI were placed in a container so that the amount of 4,4'-MDI relative to 1 mol of the tetramethylene ether diol was 6.4 mol, and the mixture was reacted at 90° C. The obtained product was dissolved in DMAc with good stirring to give a solution. Next, to the solution containing the dissolved product, a DMAc solution containing, as a chain extender, 60 mol % of EDA and 40 mol % of 1,2-PDA was added. To this solution, a DMAc solution containing, as an end-capping agent, dicyclohexylamine was further added to give a polyurethane urea solution having a polymer solid content of 25% by weight. The obtained solution at 40° C. had a viscosity of about 5400 poise. The limiting viscosity of the polymer measured in a 0.5 g/100 ml solution of DMAc at 25° C. was 1.25.

The polyurethane urea solution was extruded from a spinneret into an inert gas having a high temperature to give four filaments. The filaments were dried as passing through the high temperature gas. Before being completely dried, the filaments were led through an air jet twister so that the four filaments were twisted and coalesced. The resultant fiber was rolled up at a rate of 540 m/minute. From the coalesced four filaments, a polyurethane urea fiber having a dtex of 44 (B-b) was produced. (B-b) had a glass transition point (Tg) of −15° C. The concentration of urethane group in a polyurethane urea constituting the polyurethane urea fiber (B-b) was 0.48 mol/kg and the concentration of effective terminal amine was 29 meq/kg.

Only the polyurethane urea fiber was fed into a single cylinder knitting machine having 320 needles and a cylinder diameter of 3.5 inches (29 gauges), knitted, and steam-set at 120° C. for 1 minute to give a cylindrically knitted fabric having a width of about 5 cm (55 g/m$^2$). The obtained fabric was used as a sample without opening its width (The fabric is equivalent to two plies of a knitted fabric of 55 g/m$^2$.), and an odor removal test on nonenal was carried out. The result is shown in Table 2.

The decrease rate of nonenal in the odor removal test was 76%.

Comparative Example 1

An odor removal test on nonenal was carried out with the use of a Kynol non-woven activated carbon fiber fabric (manufactured by Nippon Kynol, Inc.) having a thickness of 3 mm. The result is shown in Table 2.

The decrease rate of nonenal in the odor removal test was 60%.

Comparative Example 2

Only a woolly nylon yarn (N) (44 dtex, 34 fil) was fed into a single cylinder knitting machine having 320 needles and a cylinder diameter of 3.5 inches (29 gauges), knitted, and steam-set at 120° C. for 1 minute to give a cylindrically knitted fabric having a width of about 5 cm (55 g/m$^2$). The obtained fabric was used as a sample without opening its width (The fabric is equivalent to two plies of a knitted fabric of 55 g/m$^2$.), and an odor removal test on nonenal was carried out. The result is shown in Table 2.

The decrease rate of nonenal in the odor removal test was 22%.

Comparative Example 3

Only a polyethylene terephthalate yarn (E) (44 dtex, 36 fil) was fed into a single cylinder knitting machine having 320 needles and a cylinder diameter of 3.5 inches (29 gauges), knitted, and steam-set at 120° C. for 1 minute to give a cylindrically knitted fabric having a width of about 5 cm (55 g/m$^2$). The obtained fabric was used as a sample without opening its width (The fabric is equivalent to two plies of a knitted fabric of 55 g/m². ), and an odor removal test on nonenal was carried out. The result is shown in Table 2.

The decrease rate of nonenal in the odor removal test was 0%.

Comparative Example 4

Polytetramethylene ether diol (PTMG) having a number average molecular weight of 1400 was used as a polyalkylene ether diol. The PTMG and 4,4'-MDI were placed in a container so that the amount of 4,4'-MDI relative to 1 mol of the PTMG was 12.5 mol, and the mixture was reacted at 80° C. The obtained product was dissolved in DMAc with good stirring. Next, to the solution containing the dissolved product, a DMAc solution containing, as a chain extender, ethylene glycol was added to give a polyurethane solution having a polymer solid content of 25% by weight. The obtained solution at 40° C. had a viscosity of about 3000 poise. The limiting viscosity of the polymer measured in a 0.5 g/100 ml solution of DMAc at 25° C. was 1.60.

The polyurethane solution was extruded from a spinneret in water to give four filaments. The filaments were dried as passing through a hot wind gas (120° C.), and rolled up at a rate of 110 m/minute. By coalescing the four filaments, a polyurethane fiber having a dtex of 44 (B-c) was produced. (B-c) had a glass transition point (Tg) of 12° C. The concentration of urethane group in a polyurethane constituting the polyurethane fiber (B-c) was 0.51 mol/kg.

Only (B-c) was fed into a single cylinder knitting machine having 320 needles and a cylinder diameter of 3.5 inches (29 gauges), knitted, and steam-set at 120° C. for 1 minute to give a cylindrically knitted fabric having a width of about 5 cm (55 g/m²). The obtained fabric was used as a sample without opening its width (The fabric is equivalent to two plies of a knitted fabric of 55 g/m².), and an odor removal test on nonenal was carried out. The result is shown in Table 2.

The decrease rate of nonenal in the odor removal test was 32%.

TABLE 2

| | | Odor removal test on nonenal (decrease rate: %, judgment) |
|---|---|---|
| Example 1 | Polyurethane urea (B-a) | 80, good |
| Example 2 | Polyurethane urea (B-b) | 76, good |
| Comparative Example 1 | Non-woven activated carbon fiber fabric | 60, poor |
| Comparative Example 2 | 6-nylon | 22, poor |
| Comparative Example 3 | Polyethylene terephthalate (E) | 0, poor |
| Comparative Example 4 | Polyurethane (B-c) | 32, poor |

<Odor Removal Test on "a Distinctive Body Odor of the Middle-Aged and Elderly" According to the Classification of Deodorant Properties by JTETC>

An odor removal test was carried with the use of, as an odor component, four components: nonenal, ammonia, acetic acid, and isovaleric acid, and a capability of removing the odor was evaluated by the following method.

Evaluation of a Capability of Removing an Odor

An instrumental analysis was carried on the four components according to the Certification Criteria of Deodorant-finished Textiles established by JTETC, and separately a sensory analysis was further carried on nonenal. Washing was carried out according to JIS L-0217-103 (1995), and then tumble-drying was carried out.

Instrumental analysis: the odor component and a sample were placed in a container and left for two hours, and then the residual concentration of the odor component was measured (the sample test concentration after two hours). The blank test concentration in the following formula was the residual concentration in a container that contained the odor component alone. A decrease rate of the odor component was calculated from the following formula. The concentrations of ammonia and acetic acid were measured by a detector tube method, and the concentrations of nonenal and isovaleric acid were measured by gas chromatography.

Decrease rate (%)=(blank test concentration after two hours−sample test concentration after two hours)/ (blank test concentration after two hours)×100

It was determined that a sample passed the test (represented by "good") when the sample satisfied all the conditions as follows: a decrease rate of nonenal was 75% or more, a decrease rate of isovaleric acid was 85% or more, a decrease rate of ammonia was 70% or more, and a decrease rate of acetic acid was 80% or more.

Sensory analysis: It was determined that a sample passed the test when five or more out of six assessors judged the odor to be faint according to the following criteria.

Strong odor: an odor is stronger than that of a reference gas for judgment.

Faint odor: an odor is equivalent to or fainter than that of a reference gas for judgment.

Example 3

As a polyurethane fiber having a glass transition point (Tg) of 0° C. or less, the polyurethane urea fiber (B-a) produced in Example 1 was used, and fibers (X) and (Y), both of which contain a carboxyl group were obtained by the following method.

A diacetate fiber having an acetylation degree of 55% (88 dtex, 24 filaments, manufactured by Mitsubishi Rayon Co., Ltd.) obtained by dry spinning according to a conventional method was graft-polymerized with a solution containing 20.0 g/l methacrylic acid, 0.6 g/l ammonium ferrous sulfate, and 0.3 g/l hydrogen peroxide with the use of an Obermaier finishing machine at a bath ratio of 1:40 at 80° C. for 60 minutes Next, the fiber was repeatedly washed alternately with water and hot water. The fiber had a graft rate of about 10% and a concentration of carboxyl group of 320 meq/kg. This fiber was referred to as (X). By the same method as the method mentioned above except that the diacetate fiber had a dtex of 150 and contained 48 filaments, a diacetate fiber (Y) containing a carboxyl group was obtained. (Y) had the same graft rate and concentration of carboxyl group as (X).

Measurement of a graft rate: A graft rate is a weight increase rate calculated from an absolute dry weight measured before the reaction (W0) and an absolute dry weight measured after the fiber was graft polymerized and washed (W1).

Graft rate=(W1−W0)×100/W0

A woven fabric was produced by the following method with the use of the polyurethane urea fiber (B-a) obtained in Example 1 and the above-mentioned (X) and (Y), and an odor removal test on a distinctive body odor of the middle-aged and elderly was carried out.

First, two polyurethane urea fibers (B-a) obtained in Example 1 were aligned parallel to each other to give a multi-end yarn (88 dtex). As a weft yarn, the multi-end yarn was covered with (X) to give a covered yarn (the covering condition: twist number=400 T/M, draft=3.0). As a warp yarn, the multi-end yarn was covered with (Y) to give a covered yarn (the covering condition: twist number=600 T/M, draft=3.5). These warp yarn and weft yarn were woven into a 2/1 twill weave (warp yarn: 90 yarns/inch, weft yarn: 106 yarns/inch) with a rapier loom, and preset at 180° C. according to a conventional method to give a woven fabric (containing 11% of the polyurethane urea fiber and 89% of the fiber containing a carboxyl group). The woven fabric was used for an odor removal test on a distinctive body odor of the middle-aged and elderly.

The results of the odor removal test on a distinctive body odor of the middle-aged and elderly is shown in Table 3. That is, the fiber satisfied all the four criteria of deodorant properties: the decrease rate of nonenal was 91%, the decrease rate of ammonia was 88%, the decrease rate of acetic acid was 86%, and the decrease rate of isovaleric acid was 88%. The fiber was a polyurethane fiber structure having a capability of removing a distinctive body odor of the middle-aged and elderly.

Comparative Example 5

A woven fabric was produced by the same method as in Example 3 except that the polyurethane fiber (B-c) produced in Comparative Example 4 was used instead of the polyurethane urea fiber (B-a), and an odor removal test on a distinctive body odor of the middle-aged and elderly was carried out. The results are shown in Table 3.

As a result of the odor removal test on a distinctive body odor of the middle-aged and elderly, the fiber failed to satisfy the criteria of deodorant properties except those of ammonia and acetic acid: the decrease rate of nonenal was 35%, the decrease rate of ammonia was 72%, the decrease rate of acetic acid was 93%, and the decrease rate of isovaleric acid was 60%. The fiber was a polyurethane fiber structure that lacks a capability of removing a distinctive body odor of the middle-aged and elderly.

Composition of a solution containing a distinctive body odor of the middle-aged and elderly: 1.0% of dibutylhydroxytoluene, 10.0% of heptanoic acid, 10.0% of octanoic acid, 15.0% of triethyl citrate containing 1% of nonenal, 2.5% of triethyl citrate containing 1% of octenal, and 61.5% of triethyl citrate, in a sum total of 100% by weight.

Six assessors having a normal sense of smell evaluated a capability of removing an odor of each of the sample compositions for cleaning air. When all the six assessors did not detect any unpleasant odor, it was determined the sample "passed" the test (represented by "good"). When one or more assessors detected an unpleasant odor, it was determined the sample "failed" the test. When one or two assessors detected an unpleasant odor, the result was represented by "fair." When three or more assessors detected an unpleasant odor, the result was represented by "poor." The results are shown in Table 4. EXAMPLE 4, EXAMPLE 5, AND COMPARATIVE EXAMPLE 6

Felt was further produced with the use of the polyurethane urea fibers (B-a) and (B-b) and the polyurethane fiber (B-c) obtained in Examples and Comparative Example mentioned above, and the felt was used for the material test of a deodorant filter.

The felt for the test was obtained by the following process.

First, raw wool was produced by cutting the polyurethane urea fibers (B-a) and (B-b), and the polyurethane fiber (B-c) obtained by any of Examples 1 and 2 and Comparative

TABLE 3

| | Deodorant capability of fabric | | | | | | |
|---|---|---|---|---|---|---|---|
| | Decrease rate of each odor component | | | | | | |
| | nonenal (%) | acetic acid (%) | iso-valeric acid (%) | ammonia (%) | nonenal Sensory analysis atmosphere | nonenal Sensory analysis fabric | judgment |
| Example 3 | 91 | 86 | 88 | 88 | Strong: 0 people Faint: 6 people | Strong: 0 people Faint: 6 people | good |
| Comparative Example 5 | 35 | 93 | 60 | 72 | Strong: 4 people Faint 2 people | Strong: 4 people Faint: 2 people | poor |

<Material Test of a Deodorant Filter>

An air filter (a polypropylene nonwoven fabric) was removed from a hot-water circulation room heater (Hitachi fan convector FU30FEA-T, manufactured by Hitachi, Ltd), and a filter material was removed out of the air filter. Instead of the filter material, felt obtained in Examples 4 and 5 and Comparative Example 6 below was attached to the air filter. The air filter was set in the heater again, and the heater was used as a circulation room heater having a deodorant filter material of the present invention.

Next, eight booths having a floor space of 15 m² and a height of 3 m were prepared as a sealed chamber where a degree of air deodorization was examined. The above-prepared heater having the filter was placed in each of the booths, and after an odor for the test was prepared, the heater was run for 6 hours/day. The odor placed in the booths was prepared as follows.

A petri dish was filled with 10 ml of a solution containing a distinctive body odor of the middle-aged and elderly having the following composition, and the petri dish was left in the booth for 60 minutes.

Example 4. The volume of the raw wool was increased with a needle, and the raw wool was heat-pressed at 100° C. to give felt consisting of the polyurethane urea fiber and the polyurethane fiber, and having a thickness of 1 mm and a permeability of 100 cc/cm²·second. The permeability was adjusted by controlling the volume through needle-punching. The obtained felt was used as the deodorant filter material. As a result of the test, it is clear from Table 4 that both of the air cleaning filter comprising (B-a) (Example 4) and the air cleaning filter comprising (B-b) (Example 5) were able to remove an unpleasant odor, and that the filters had a long, notably excellent effective period, which was 10 days or more.

As a result of the material test of the deodorant filter as mentioned above, it was determined that both of the filter with the use of the polyurethane fiber obtained in Example 1 and the filter with the use of the polyurethane fiber obtained in Example 2 passed the test for a capability of removing an odor, and that the filter with the use of the polyurethane fiber (B-c) obtained in Comparative Example 4 failed the test for a capability of removing an odor (Comparative example 6).

TABLE 4

| | Material test of a deodorant filter | | | | | | | | | | | |
|---|---|---|---|---|---|---|---|---|---|---|---|---|
| | Day 1 | Day 2 | Day 3 | Day 4 | Day 5 | Day 6 | Day 7 | Day 8 | Day 9 | Day 10 | Day 15 | Day 20 |
| Example 4 | Good | Good | Good | Good | Good | Good | Good | Good | Good | Good | Good | Good |
| Example 5 | Good | Good | Good | Good | Good | Good | Good | Good | Good | Good | Good | Fair |
| Comparative Example 6 | Fair | Poor | Poor | Poor | Poor | Poor | Poor | Poor | Poor | Poor | — | — |

Good: passed the test, all the six assessors did not detect any unpleasant odor
Fair: failed the test, one or two assessors detected an unpleasant odor
Poor: failed the test, three or more assessors detected an unpleasant odor.

The invention claimed is:

1. A method of removing the odor of nonenal, comprising contacting nonenal with a deodorant material comprising a polyurethane fiber, wherein the glass transition point (Tg) of the polyurethane fiber is −100 to 0° C. and the polyurethane fiber comprises the reaction product of a polymer diol, a diisocyanate, and as a chain extender, a diamino compound or a low molecular weight diol, wherein the polyurethane fiber is effective to remove nonenal odor, wherein the polymer diol is a copolymerized diol compound comprising formula (I):

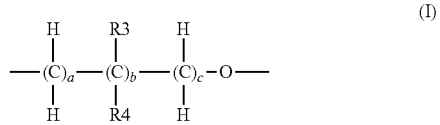

(I)

wherein a and c is an integer of 1 to 3, b is an integer of 0 to 3, and R3 and R4 each are a hydrogen atom or an alkyl group having 1 to 3 carbon atoms;
the diisocyanate is selected from the group consisting of diphenylmethane diisocyanate, tolylene diisocyanate, 1,4-diisocyanate benzene, xylylene diisocyanate, 2,6-naphthalene diisocyanate, methylenebis(cyclohexyl isocyanate), isophorone diisocyanate, methylcyclohexane-2,4-diisocyanate, methylcyclohexane-2,6-diisocyanate, cyclohexane-1,4-diisocyanate, hexahydroxylylene diisocyanate, hexahydrotolylene diisocyanate, and octahydro-1,5-naphthalene diisocyanate;
the diamino compound is selected from the group consisting of ethylenediamine, 1,2-propanediamine, 1,3-propanediamine, hexamethylenediamine, p-phenylenediamine, p-xylylenediamine, m-xylylenediamine, p,p'-methylenedianiline, 1,3-cyclohexyldiamine, hexahydro-meta-phenylenediamine, 2-methylpentamethylenediamine, and bis(4-aminophenyl)phosphine oxide;
the low molecular weight diol is selected from the group consisting of ethylene glycol, 1,3-propanediol, 1,4-butanediol, bishydroxyethoxy benzene, bishydroxyethylene terephthalate, and 1-methyl-1,2-ethane diol;
and the concentration of urethane group in a polyurethane constituting the polyurethane fiber is about 0.2 to 3.5 mol/kg.

2. The method according to claim 1, wherein the polyurethane fiber is further capable of removing the odor of at least one selected from the group consisting of ammonia, acetic acid, and isovaleric acid.

3. The method according to claim 1, wherein the polyurethane fiber is a polyurethane urea fiber.

4. The method according to claim 1, wherein the deodorant material further comprises a fiber containing a carboxyl group.

5. The method according to claim 4, wherein the fiber containing a carboxyl group has a concentration of carboxyl group of 30 to 3000 meq/kg.

6. The method according to claim 4, wherein the fiber containing a carboxyl group is a cellulose fiber graft-polymerized with 2 to 30% by weight of a hydrophilic vinyl monomer.

7. The method according to claim 1, wherein the melting point of the polyurethane fiber is 150 to 300° C.

8. The method according to claim 1, wherein the concentration of effective terminal amine in a polyurethane constituting the polyurethane fiber is 15 to 50 meq/kg.

* * * * *